United States Patent
Pandey et al.

(10) Patent No.: US 7,147,840 B2
(45) Date of Patent: Dec. 12, 2006

(54) OXO-BACTERIOPYROPHEOPHORBIDE-A CARBOXYLIC ACID AND ESTERS THEREOF

(75) Inventors: Ravindra K. Pandey, Williamsville, NY (US); Andrei Kozyrev, Goleta, CA (US); Xiang Zheng, Cheektowaga, NY (US)

(73) Assignee: Health Research, Inc., Buffalo, NY (US)

( * ) Notice: Subject to any disclaimer, the term of this patent is extended or adjusted under 35 U.S.C. 154(b) by 48 days.

(21) Appl. No.: 11/066,511

(22) Filed: Feb. 25, 2005

(65) Prior Publication Data

US 2006/0111565 A1    May 25, 2006

Related U.S. Application Data

(60) Provisional application No. 60/630,688, filed on Nov. 24, 2004.

(51) Int. Cl.
  *A61B 5/055*    (2006.01)
(52) U.S. Cl. ............... 424/9.362; 424/9.61; 540/145; 534/15; 514/185; 514/410
(58) Field of Classification Search ............. 424/9.362, 424/9.61; 540/145; 534/15; 514/185, 410
  See application file for complete search history.

(56) References Cited

U.S. PATENT DOCUMENTS 5,770,730 A    6/1998    Pandey et al. ............... 540/472
6,103,751 A    8/2000    Pandey et al. ............... 514/410

FOREIGN PATENT DOCUMENTS

WO    WO 95/32206    5/1994

OTHER PUBLICATIONS

A.N. Kozyrev, T.J. Dougherty and R.K. Pandey, "LiOH Promoted Allomerization of Pyropheophorbide-a. A Convenient Synthesis of 132-Oxopyropheophorbide-a and its Unusual Enolization," Chem. Commun. (1998) 481-482.
S. Mettah, T.J. Dougherty, R.K. Pandey, "Cycloaddition Reaction on 3-Vinylemeraldins: Formation of Unexpected Porphyrins with Seven-Membered Exocyclic Ring Systems," Tetrahedron Letters 40 (1999) 6171-6175.
G. Zheng, W.R. Potter, S.H. Camacho et al., "Synthesis, Photophysical Properties, Tumor Uptake and Preliminary In vivo Photosensitizing Efficacy of a Homolgous Series of 3-(1'-Alkyloxy)ethyl-3-devinylpurpurin-18-N-alkylimides with Variable Lipophilicity," Journal of Medical Chemistry 44 (2001) 1540-1559.
A.N. Kozyrev, G. Zheng, E. Lazarou, T.J. Dougherty, K.M. Smith, R.K. Pandey, "Synthesis of Emeraldin and Purpurin-18 Analogs as Target-Specific Agents for Photodynamic Therapy," Tetrahedron Letters 38: 19 (1997) 3335-3338.
A.N. Kozyrev, G. Zheng, T. Dougherty, K.M. Smith, R.K. Pandey, "Synthesis of Stable Bacteriopurpurin-a Derivatives as Potential Sensitizers for Photodynamic Therapy," Tetrahedron Letters 37:36 (1996) 6431-6474.
Y. Chen, A. Graham, W. Potter, R. Pandey, T. Dougherty et al., "Bacteriopurpurinimides: Highly Stable and Potent Photosensitizers for Photodynamic Therapy," Journal of Medicinal Chemistry 45 (2002) 255-258.
A.N. Kozyrev, J.D. Alderfer, B.C. Robinson, "Prazolinyl and Cyclopropyl Derivatives of Protoporphyrin IX and Chlorins Related to Chlorophyll a," Tetrahedron 59 (2003) 499-504.

(Continued)

*Primary Examiner*—James O. Wilson
*Assistant Examiner*—Jason H. Johnsen
(74) *Attorney, Agent, or Firm*—Michael L. Dunn

(57) ABSTRACT

A compound having the structural formula:

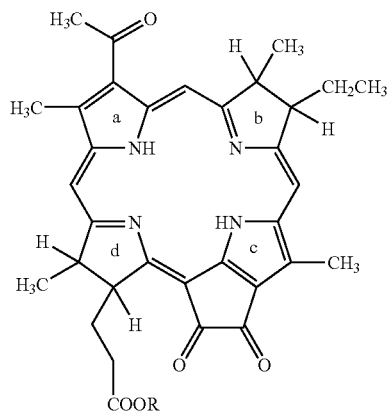

where R is H or lower alkyl of 1 through 12 carbon atoms. In general, the compounds of the invention are $13^2$-Oxo-bacteriopyropheophorbide—a carboxylic acid and $C_1$–$C_{12}$ alkyl esters thereof. A method for the preparation of the carboxylic acid compounds of the invention includes the step of reacting bacteriopyropheophorbide—a alkyl ester with lithium hydroxide tetrahydrofuran and water. A method of the invention for the preparation of the $C_1$–$C_{12}$ alkyl ester compounds of the invention includes the steps of reacting bacteriopyropheophorbide—a alkyl, especially methyl, ester with lithium hydroxide in tetrahydrofuran and water to obtain $13^2$-Oxo-bacterio-pyropheophobide-a carboxylic acid followed by reacting the carboxylic acid with an acid chloride producing reagent to obtain the $13^2$-Oxo-bacterio pyropheophobide-a acid chloride (compound 5) and reacting the $13^2$-Oxo-bacterio pyropheophobide-a acid chloride with a $C_1$–$C_{12}$ alcohol to obtain a $13^2$-Oxo-bacterio-pyropheophobide-a carboxylic acid $C_1$–$C_{12}$ alkyl ester (compound 6). The compounds of the invention may be used as long wavelength absorbing photosensitizers for photodynamic therapy.

10 Claims, 5 Drawing Sheets

OTHER PUBLICATIONS

A.N. Kozyrev, V. Suresh, S. Das, M.O. Senge, M. Shibata, T.J. Dougherty, and R. Pandey, "Syntheses and Spectroscopic Studies of Novel Chlorins with Fused Quinoxaline or Benzimidazole Ring Systems and the Related Dimers with Extended Conjugation," Tetrahedron 56 (2000) 3353-3364.

A.N. Kozyrev, J.L. Alderfer, T.J. Dougherty, and R.K. Pandey, "Synthesis of Verdinochlorins: a New Class of Long-Wavelength Absorbing Photosensitizers," Chem. Commun. (1998) 1083-1084.

A.F. Mironov, A.N. Kozyrev, A.S. Brandis, "Sensitizers of Second Generation for Photodynamic Therapy of Cancer Based on Chlorophyll and Bacteriochlorophyll Derivatives," Proc. SPIE, 1992, 202-204.

A.G. Mironov, A.N. Kozyrev, P. Yu.Perepyolkin, "New Sensitizers for Diagnosis and Photodynamic Therapy of Malignant Tissues," Proc. SPIE, 1993, 186-192.

A.N. Kozyrev, A.V. Efimov, O.A. Efremova, P. Yu.Perepyolkin, "New Chlorin and Bacteriochlorine-Type Photosensitizers for Photodynamic Therapy," Proc. SPIE, 1994, 297-305.

OXO-BACTERIOPYROPHEOPHORBIDE-A CARBOXYLIC ACID AND ESTERS THEREOF

This application claims the benefit under 35 U.S.C. §119(e) of U.S. Provisional Application No. 60/630,688, filed Nov. 24, 2004.

STATEMENT REGARDING FEDERALLY SPONSORED RESEARCH

This invention was made with funding from the National Institute of Health Grant Number NIH CA55791. The United States Government may have certain rights in this invention.

BACKGROUND OF THE INVENTION

1. Field of the Invention

This invention relates to new stable bacteriochlorins generally having long wave length absorptions between 700 and 800 nm. Such compounds have utility as photsensitizers for photodynamic therapy (PDT).

2. History of the Prior Art

PDT has emerged as one of the promising strategies in cancer treatment. In this therapy, patients are given intravenous injections of a porphyrin-based drug that accumulates in cancer cells in generally higher concentrations than in surrounding tissue. The photosensitizing agent is then activated by a visible or near IR light to cancer sites through fiber optics which following energy transfer to molecular oxygen produces the singlet oxygen, the putative cytotoxic agent. PDT is thus a novel and potentially important form of cancer therapy. At presents efforts are underway in various laboratories to prepare photosensitizers exhibiting long wavelength absorption near 700–800 nm, which could enable to treat large tumors due to deeper light penetration in tissues at that wavelength. Therefore, during last ten years a variety of naturally occurring bacteriochlorins (porphyrin systems in which two pyrrole rings diagonal to each other are reduced) have been synthesized and evaluated for PDT efficacy. Unfortunately, most of the naturally occurring bacteriuochlorins (e.g. bacteriochlorophyll-a) are not stable in vivo and slowly convert into chlorin systems.

BRIEF DESCRIPTION OF THE INVENTION

An object of the present invention is to convert bacteriochlorophyl-a into a stable analog having desired long wavelength absorption and other desirable photophysical and photosensitizing characteristics.

The compounds of the invention are $13^2$-Oxo-bacteriopyropheophorbide-a carboxylic acid and $C_1$–$C_{12}$ alkyl esters thereof.

In accordance with the invention, a method for the preparation of the carboxylic acid compounds of the invention includes the step of reacting bacteriopyropheophorbide-a alkyl ester with lithium hydroxide in tetrahydrofuran and water.

A method of the invention for the preparation of the $C_1$–$C_{12}$ alkyl ester compounds of the invention includes the steps of reacting bacteriopyropheophorbide-a alkyl, especially methyl, ester with lithium hydroxide in tetrahydrofuran and water to obtain $13^2$-Oxo-bacterio-pyropheophobide-a carboxylic acid followed by reacting the carboxylic acid with an acid chloride producing reagent to obtain the $13^2$-Oxo-bacterio-pyropheophobide-a acid chloride (compound 5) and reacting the $13^2$-Oxo-bacterio pyropheophobide-a acid chloride with a $C_1$–$C_{12}$ alcohol to obtain a $13^2$-Oxo-bacterio-pyropheophobide-a carboxylic acid $C_1$–$C_{12}$ alkyl ester (compound 6). The acid chloride producing reagent is thionyl chloride, phosphorous trichloride, phosphorous pentachloride or oxylyl chloride.

A method for the specific preparation of the methyl ester compound of the invention from bacteriopyropheophorbide-a alkyl ester, without forming an intermediate acid chloride, is by reacting bacteriopyropheophorbide-a alkyl ester (compound 2) with lithium hydroxide in tetrahydrofuran and water to obtain $13^2$-Oxo-bacterio-pyropheophobide-a carboxylic acid (compound 3) followed by reacting the carboxylic acid with methyl azide ($CH_2N_2$) to directly obtain a $13^2$-Oxo-bacterio-pyropheophobide-a carboxylic acid methyl ester (compound 4).

In accordance with the invention, a compound is therefore provided having the structural formula:

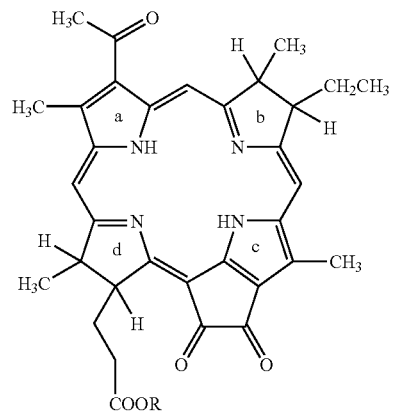

where R is H or lower alkyl of 1 through 12 carbon atoms.

The compounds of the invention may be used as long wavelength absorbing photosensitizers for photodynamic therapy.

DETAILED DESCRIPTION OF THE INVENTION

Figure 1:
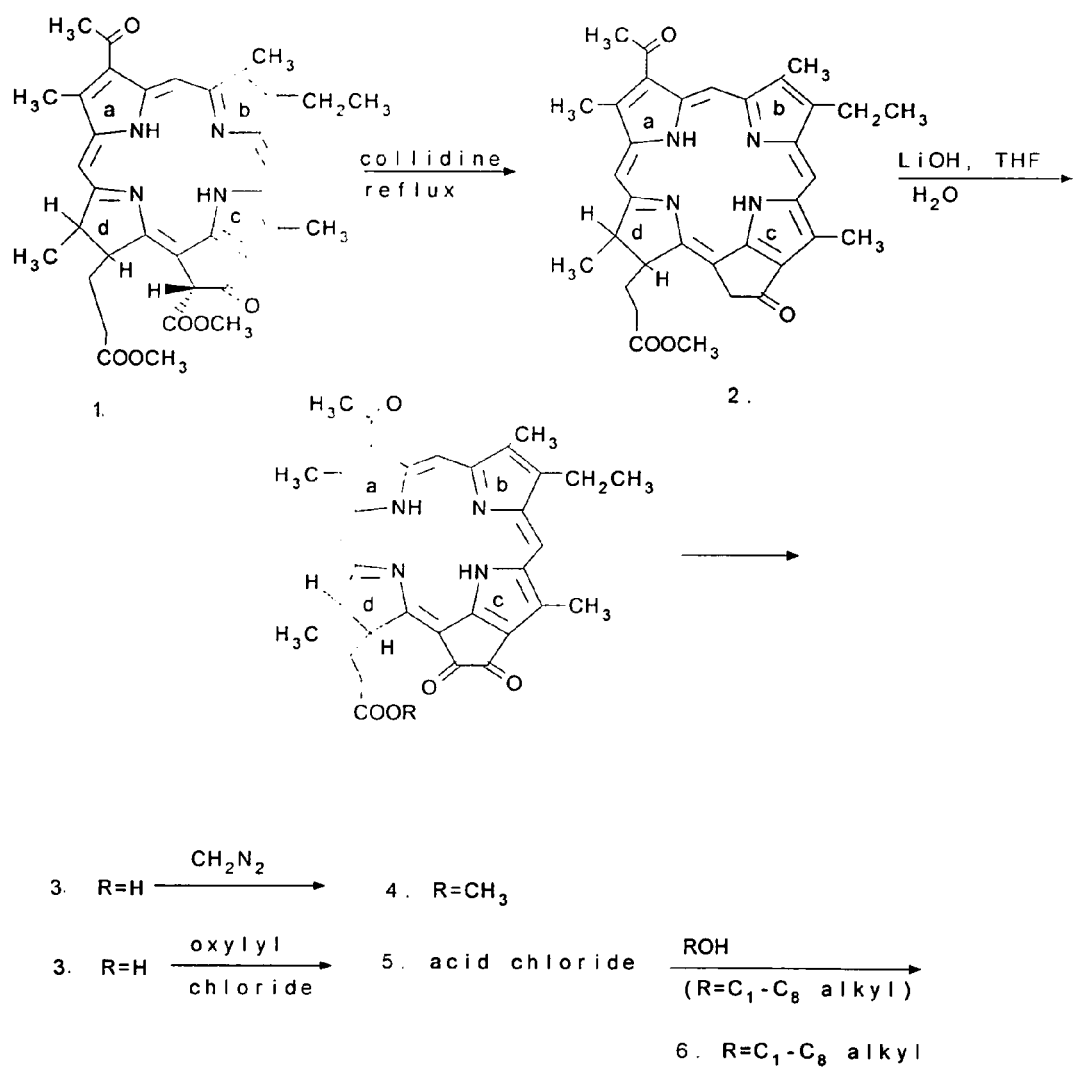
FIG. 1 is a schematic equation showing preparation of bacteriopyropheophorbide-a alkyl ester and $13^2$-oxo-bacteriopyropheophorbide-a carboxylic acid and corresponding esters.
Figure 2:
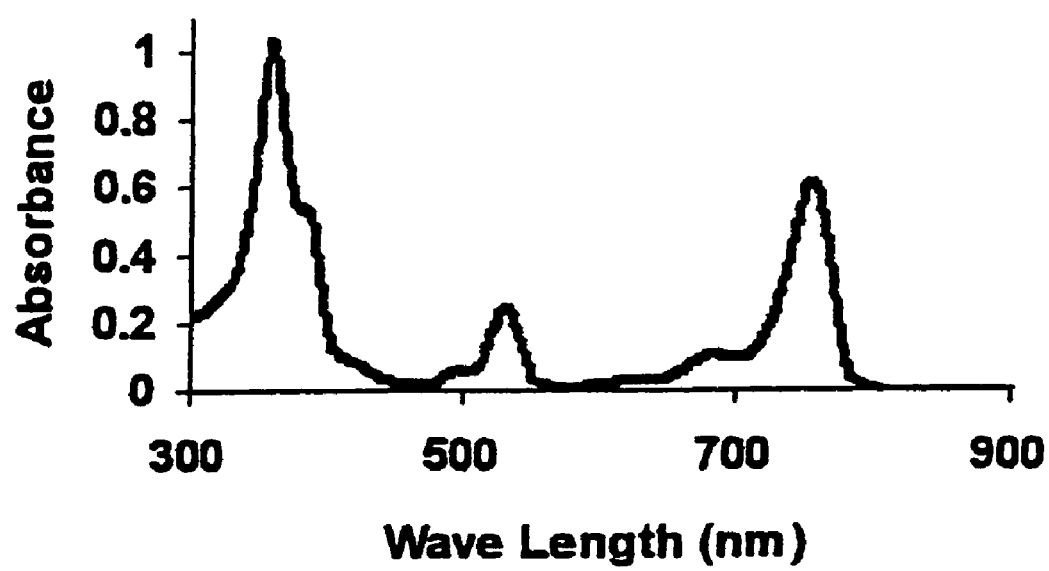
FIG. 2 is a graph showing the absorption curve of light for bacteriopyropheophorbide-a methyl ester. (compound 2).
Figure 3:
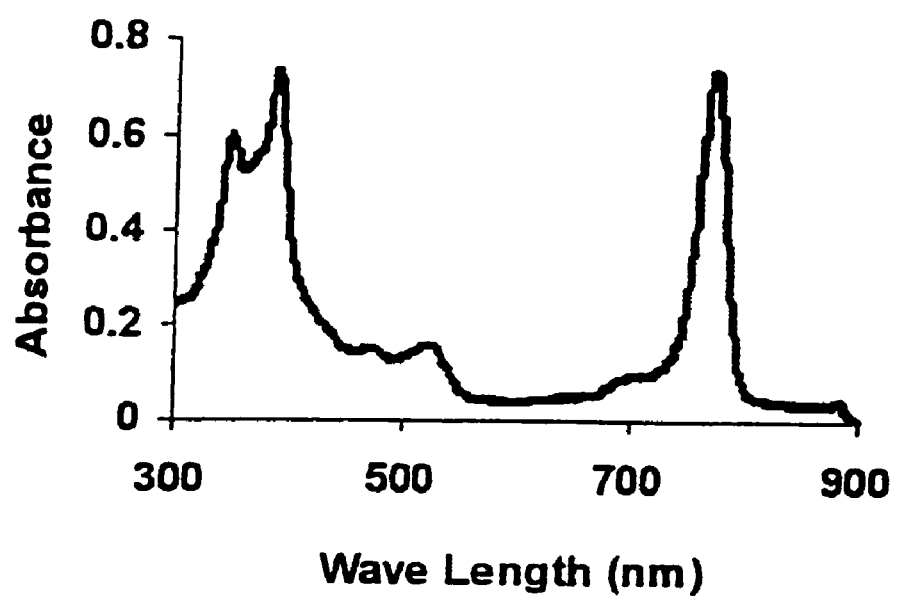
FIG. 3 is a graph showing the absorption curve of light for $13^2$-Oxo-bacteriopyropheophorbide-a carboxylic acid methyl ester. (compound 4).

Bacteriopheophorbide-a methyl ester 1 (315 mg) was obtained from *Rb. sphaeroides* by known methods. As shown in FIG. 1, it was dissolved in collidine (20 ml) and refluxed under nitrogen for 2 hrs. Collidine was removed by rotavapor under high vacuum (55° C. bath). Hexane was added. The precipitate was filtered off and washed with hexane. The precipitate was dissolved in dichloromethane, chromatographed on silica (eluent: 3%→4% Acetone in dichloromethane) and the desired bacteriopyropheophorbide-a 2 was isolated as the major product. TLC: 4% Acetone in Dichlormethane. Yield: 180 mg (63%). Light absorbance of compound 2 was determined at various wavelengths of light as shown in FIG. 2. NMR (AMX400): 8.99, 8.48, and 8.43 (each s, 1H, 5-H, 10-H and 20-H); 5.10 (m, 1H, 17-H); 4.93 (m, 1H, 7-H); 4.30 (m, 2H, 8-H and 18-H); 4.14 and 4.04 (m, 2H, 13$^2$-H); 3.62 (s, 3H, 17-CO$_2$CH$_3$); 3.50 (s, 3H, 3-CH$_3$); 3.45 (s, 3H, 12-CH$_3$); 3.17 (s, 3H, 2-CH$_3$); 2.59 (m, 2H, 17$^2$-CH$_2$); 2.32 and 2.25 (each m, 3H, 8$^1$-CH$_2$ and 17$^1$-CH$_2$); 2.10 (m, 1H, 17$^1$-CH$_2$); 1.81 (d, 3H, 18-CH$_3$); 1.77 (d, 3H, 7-CH$_3$); 1.12 (t, 3H, 8$^2$-CH$_3$); 0.35 and −1.03 (each s, 1H, 2NH).

Preparation of 13$^2$-Oxo-bacteriopyropheophorbide-a Carboxylic Acid 3 and the Corresponding Methyl Ester 4:

Bacteriochlorin 2 (50 mg) was dissolved in THF (10 ml) and a suspension of LiOH (80 mg) in water (1 ml) was added to the solution. The reaction mixture was exposed to air and vigorously stirred for 24 hrs at room temperature, then 1% (v/v) AcOH water solution (70 ml) was added. The product was extracted with dichloromethane/THF mixture (1:1, 50 ml+25 ml). The combined extracts were washed with water (50 ml×2), dried over sodium sulfate and the solvent was evaporated. The intermediate product, mainly containing the corresponding carboxylic acid 3 was dissolved in dichloromethane/THF mixture (1:1, 20 ml), and briefly treated with excess of diazomethane (400 mg Diazald, 3 pellets KOH, 5 ml EtOH, 0.5 ml H$_2$O, 3 ml Ether). The conversion of carboxylic acid to the corresponding methyl ester was monitored by TLC. A few drops of acetic acid were then added to decompose the excess of diazomethane. The reaction mixture was washed with water and the solvent was evaporated under vacuum. The residue was purified by preparative plates (hexane/dichloromethane/acetone=5:10:2), or by silica column (5% →8% acetone in dichloromethane) and was obtained in 39% yield (20 mg). $^1$H-NMR (600 MHz): 9.53, 8.99 and 8.92 [each s, 1H (5-H, 10-H and 20-H)]; 5.02 (m, 1H, 7-H); 4.53 (m, 2H, 8-H and 17-H); 4.29 (m, 1H, 18-H); 3.69 (s, 3H, 17-CO$_2$CH$_3$); 3.65 (s, 3H, 3-CH$_3$); 3.59 (s, 3H, 12-CH$_3$); 3.24 (s, 3H, 2-CH$_3$); 2.72 (m, 1H, 17$^2$-CH$_2$); 2.65 (m, 17$^1$-CH$_2$); 2.34 and 2.32 (each m, 2H, 8$^1$–CH$_2$); 2.17 (m, 1H, 17$^1$–CH$_2$); 1.90 (d, 3H, 18-CH$_3$); 1.81 (d, 3H, 7-CH$_3$); 1.15 (t, 3H, 8$^2$-CH$_3$); −0.39 and −2.11 (each s, 1H, 2NH).

In vitro Photosensitizing Efficacy:

Cells were plated in 96 well plates in complete media. After overnight incubation to allow the cells to attach, the compound 4 was added at various concentrations. After 24 hrs incubation in the dark at 37° C. The cells were irradiated with laser light source at 768 nm wavelength. After laser treatment, medium was replaced with fresh medium. The cells were incubated for 48 hrs. Then 10 μl of 4 mg/ml solution of 3-[4,5-dimethylthiazol-2-yl]-2,5-diphenyl tetrazolium-bromide (MTT) dissolved in PBS was added to each well. After 4 hrs incubation at 37° C. the medium was removed and 100 μl dimethyl sulphoxide (DMSO) was added to each well to dissolve the formazin crystals. The plates were read on a microtiter plate reader (Miles Inc. Titertek Multiscan Plus MK II) at an absorbance of 560 nm.

The results were plotted as percent survival of the corresponding dark (drug no light) control for each photosensitizer tested.

Figure 4:
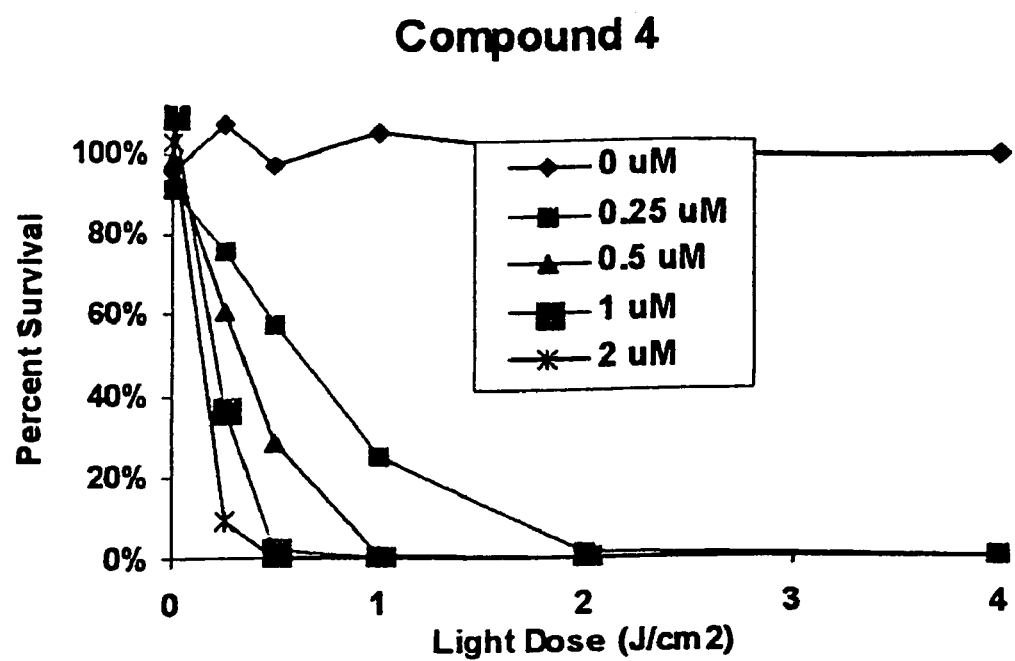
FIG. 4 is a graph showing percent survival of RIF tumor cells at various concentrations of $13^2$-oxo-bacteriopyropheophorbide-a carboxylic acid methyl ester upon exposure to light at various energy levels at a wavelength of 768 nm.
Figure 5:
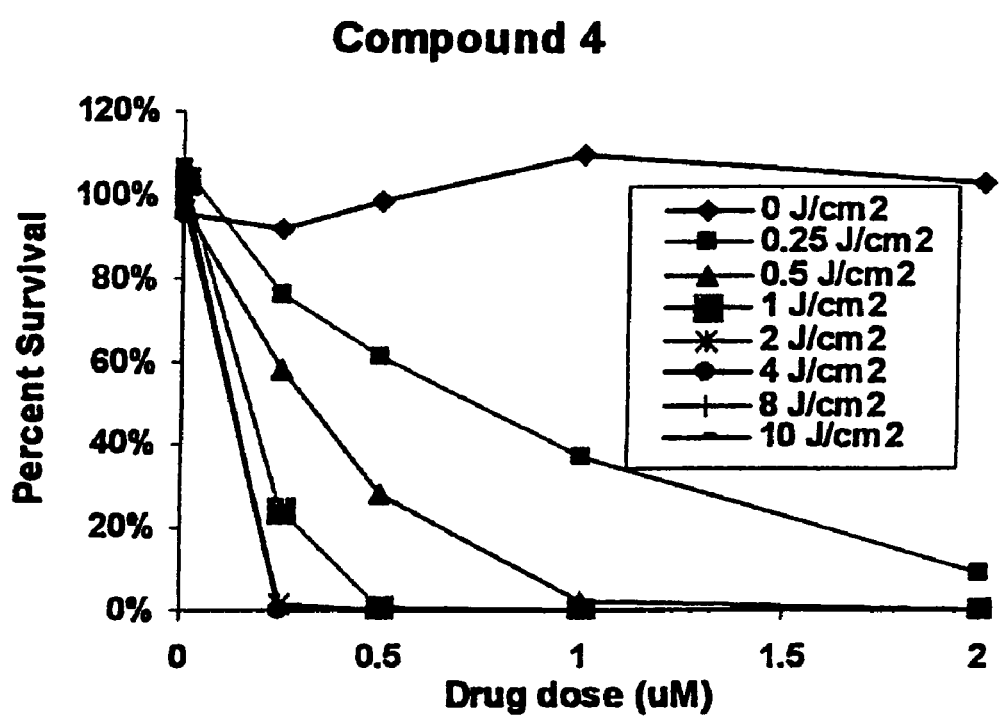
FIG. 5 is a graph showing percent survival of RIF tumor cells at various energy levels of light at a wavelength of 768 nm. against various drug dose concentrations.

The photosensitizing efficacy of bacteriochlorin 4 was performed at variable drug and light doses. The results are is summarized in FIGS. 4 and 5.

What is claimed is:

1. A compound of the formula:

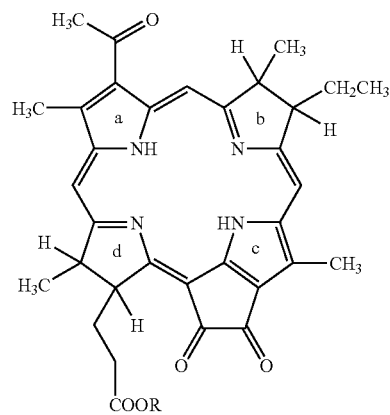

where R is H or lower alkyl of 1 through 12 carbon atoms.

2. The compound 13$^2$-Oxo-bacteriopyropheophorbide-a carboxylic acid.

3. The compound 13$^2$-Oxo-bacteriopyropheophorbide-a carboxylic acid C$_1$–C$_{12}$ alkyl ester.

4. The compound of claim 3 where the alkyl ester is a C$_1$–C$_8$ alkyl ester.

5. The compound of claim 3 where the alkyl ester is a methyl, ethyl or propyl ester.

6. A method for the preparation of the compound of claim 1 where R is hydrogen by reacting bacteriopyropheophorbide-a alkyl ester with lithium hydroxide in tetrahydrofuran and water.

7. A method for the preparation of the compound of claim 1 where R is lower alky of 1–12 carbon atoms by reacting bacteriopyropheophorbide-a alkyl ester with lithium hydroxide in tetrahydrofuran and water to obtain 13$^2$-Oxo-bacterio-pyropheophobide-a carboxylic acid followed by reacting the carboxylic acid with an acid chloride producing reagent to obtain the 13$^2$-Oxo-bacterio pyropheophobide-a acid chloride and reacting the 13$^2$-Oxo-bacterio pyropheophobide-a acid chloride with a C$_1$–C$_{12}$ alcohol to obtain a 13$^2$-Oxo-bacteriopyropheophobide-a carboxylic acid C$_1$–C$_{12}$ alkyl ester.

8. The method of claim 7 where the acid chloride producing reagent is selected from the group consisting of thionyl chloride, phosphorous trichloride, phosphorous pentachloride and oxylyl chloride.

9. The method of claim 8 where the acid chloride producing reagent is oxylyl chloride.

10. A method for the preparation of the compound of claim 1 where R is methyl by reacting bacteriopyropheophorbide-a alkyl ester with lithium hydroxide in tetrahydrofuran and water to obtain 13$^2$-Oxo-bacterio-pyropheophobide-a carboxylic acid followed by reacting the carboxylic acid with methyl azide to obtain a 13$^2$-Oxo-bacterio-pyropheophobide-a carboxylic acid methyl ester.

* * * * *